(12) United States Patent
Zhang et al.

(10) Patent No.: US 8,785,680 B2
(45) Date of Patent: Jul. 22, 2014

(54) ANTIMICROBIAL COMPOUNDS AND USES THEREOF

(75) Inventors: Lianhui Zhang, Singapore (SG); Yinyue Deng, Singapore (SG); Jien Wu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/697,993

(22) PCT Filed: May 12, 2011

(86) PCT No.: PCT/SG2011/000183
§ 371 (c)(1),
(2), (4) Date: Jan. 28, 2013

(87) PCT Pub. No.: WO2011/142724
PCT Pub. Date: Nov. 17, 2011

(65) Prior Publication Data
US 2013/0131172 A1     May 23, 2013

Related U.S. Application Data

(60) Provisional application No. 61/334,727, filed on May 14, 2010.

(51) Int. Cl.
*C07C 61/00*     (2006.01)
(52) U.S. Cl.
USPC ........................................................ 562/400
(58) Field of Classification Search
USPC .................... 514/557, 560; 562/400
See application file for complete search history.

(56) References Cited

U.S. PATENT DOCUMENTS

| | | | |
|---|---|---|---|
| 3,163,669 A | 12/1964 | Stilz et al. | |
| 3,177,226 A | 4/1965 | Stilz et al. | |
| 3,493,590 A | 2/1970 | Chabardes | |
| 4,575,512 A * | 3/1986 | Hall et al. | 514/469 |
| 4,699,920 A * | 10/1987 | Skuballa et al. | 514/530 |
| 7,459,451 B2 * | 12/2008 | Abe et al. | 514/234.2 |
| 7,799,782 B2 * | 9/2010 | Munson et al. | 514/234.5 |

FOREIGN PATENT DOCUMENTS

WO     WO 03/039529     5/2003

OTHER PUBLICATIONS

Hall et al. CAS: 105: 42538, 1986.*
Skuballa et al. CAS: 104: 168255, 1986.*
Montecatini's CAS: 61: 47498, 1964.*
International Search Report and Written Opinion, mailed Jun. 29, 2011, for Application No. PCT/SG2011/000183.
International Preliminary Report on Patentability, mailed Nov. 29, 2012, for Application No. PCT/SG2011/000183.
He et al., Genome scale analysis of diffusible signal factor regulon in *Xanthomonas campestris* pv. Campestris: identification of novel cell-cell communication-dependent genes and functions. *Mol Microbiol*. 2006;59(2):610-22.
Mahenthiralingam et al., DNA-based diagnostic approaches for identification of *Burkholderia cepacia complex*, *Burkholderia vietnamiensis*, *Burkholderia multivorans*, *Burkholderia stabilis*, and *Burkholderia cepacia* genomovars I and III. *J Clin Microbiol*. 2000;38(9):3165-73.
Rose et al., Biocide susceptibility of the *Burkholderia cepacia complex*. *J Antimicrob Chemother*. 2009;63(3):502-10.
Rossignol et al., CandidaDB: a multi-genome database for *Candida* species and related Saccharomycotina. *Nucleic Acids Research*. 2008;36:D557-D561.
Shimo et al., Studies on search of new antimicrobial active compound for food preservation: I. unsaturated fatty acids and their derivatives. *Shokuhin Eiseigaku Zasshi*. Feb. 1966;7(1):55-9.
Taber et al., Potassium hydride in paraffin: a useful base for organic synthesis. *J Org Chem*. 2006;71:8973-4.
Tsukada et al., Palladium-catalyzed allylic alkenylation of allylic alcohols with n-butyl acrylate. *Chem Comm*. 2003;19:2404-5.
Wang et al., A bacterial cell-cell communication signal with cross-kingdom structural analogues. *Mol Microbiol*. 2004;51(3):903-12.
Extended European Search Report for EP 11780893.1, mailed Feb. 24, 2014.
Boon et al., A novel DSF-like signal from Burkholderia cenocepacia interferes with Candida albicans morphological transition. ISME J. Jan. 2008;2(1):27-36. Epub 2007 Nov 29.
Christie et al., Synthesis and characterization of the complete series of methylene-interrupted cis,cis-octadecadienoic acids. Chem Phys Lipids. 1967;1:407-23.
Dzhemileva et al., Oxidation of polyunsaturated ethers and esters by molecular oxygen catalyzed by palladium salts. Bulletin of the Academy of Sciences of the USSR; Division of Chemical Sciences. Feb. 1, 1983;32(2):307-12.
Galera et al., Insect growth regulators. III synthesis of JH-3 analogs substituted in 5-or 7-position. Bulletin de l'Academie Polonaise de Sciences. Jan. 1, 1978;26(6):427-39.
Heslinga et al., Synthesis of 2trans-alkene-mono-and—poly-ynoic acids with a triple bond in the 5-position and their hydrogenation. A new synthesis of arachidonic acid. Recueil des Travaux Chimiques des Pays-Bas. Sep. 2, 1973;92(3):287-303.
Higgs, Antimicrobial components of the red alga laurencia hybrid (rhodophyta, rhodomelaceae). Jan. 1, 1981;37(24):4255-8.
Raghavan et al., Stereoselective synthesis of the enantiomer of the key fragment of crocain. Tetra Lett. Jul. 12, 2004;45(29):5593-5.
Trost et al., Ruthenium catalyzed synthesis of butenolides and pentenolides via contra-electronicα-alkylation of hydroxyalkynoates. J Am Chem Soc. Feb. 1, 1995;117(7):1888-99.
Dzhemilev et al., Insect pheromones and their analogs. III. Synthesis of the sex attractants of some lepidoptera. *Chem Nat Comp*. Jan. 1, 1980; 82-5.

* cited by examiner

*Primary Examiner* — Rei-tsang Shiao
(74) *Attorney, Agent, or Firm* — Wolf, Greenfield & Sacks, P.C.

(57) ABSTRACT

The present invention relates to novel antimicrobial compounds, methods of their production as well as uses thereof.

4 Claims, 5 Drawing Sheets a b a)

b)

ANTIMICROBIAL COMPOUNDS AND USES THEREOF

CROSS-REFERENCE TO RELATED APPLICATIONS

The present application is a national stage filing under 35 U.S.C. §371 of international PCT application, PCT/SG2011/000183, filed May 12, 2011, which claims priority under 35 U.S.C. §119(e) to U.S. provisional application, U.S. Ser. No. 61/334,727, filed May 14, 2010; each of which is incorporated herein by reference.

FIELD OF THE INVENTION

The present invention relates to novel antimicrobial compounds, methods of their production as well as uses thereof.

BACKGROUND OF THE INVENTION

Antibiotics, which act by either killing or stopping microbial growth, have been used extensively in the control and prevention of infectious diseases. However, this live-or-die selection pressure has inevitably fostered the emergence of superbugs that are resistant to multidrugs. Infections associated with antibiotic-resistant pathogens are increasingly common in clinical and nosocomial settings (Pfaller et al., 1998; Livermore, 2004). Such infections have become a serious public health concern. In addition, it is known that bacterial pathogens can form biofilms, in which single-celled bacteria individually interconnect with each other through extracellular matrix. The biofilm bacterial cells could escape the human defense responses and withstand a high dose of antibiotics (Costerton et al., 1995).

When a pathogen encounters host organisms, whether it can establish infection or not is determined by the outcome of host-pathogen interactions. It is believed that any molecule that could fundamentally alter the balance between the host defense mechanisms and the pathogen virulence in favor of the host might be of practical value to prevent and control pathogenic infections (Zhang and Dong, 2004). Therefore, there remains a need to develop new treatments for the control and prevention of microbial infections.

SUMMARY OF THE INVENTION

In one aspect the invention relates to compounds of formula (I)

(I)

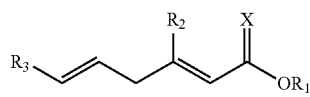

wherein
X is a carbon or heteroatom;

$R^1$, $R^2$ and $R^3$ are each independently selected from the group consisting of hydrogen, unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy, unsubstituted or substituted $C_6$-$C_{14}$ aryl, an unsubstituted or substituted 5- to 10-membered heteroaryl wherein 1 to 4 ring atoms are independently selected from nitrogen, oxygen or sulfur, an unsubstituted or substituted 5- to 10-membered heteroalicyclic ring wherein 1 to 3 ring atoms are independently nitrogen, oxygen or sulfur, —C(O)R, —C(O)OR, —C(O)NRR', —NRR', $—S(O)_2R$, $—S(O)_2OR$, and $—S(O)_2NRR'$, R and R' are independently selected from the group consisting of hydrogen and unsubstituted or substituted $C_1$-$C_{10}$ alkyl, unsubstituted or substituted $C_1$-$C_{10}$ alkenyl, unsubstituted or substituted $C_1$-$C_{10}$ alkynyl;

or a tautomer, geometrical isomer, enantiomer, diastereomer, racemate form, pharmaceutically acceptable salt or prodrug thereof.

In another aspect, the invention relates to compositions comprising the compounds of the invention.

In a further aspect, the invention is directed to compounds of the invention for use as a medicament, such as an antibacterial agent or antibiotic or an anti-fungal agent.

In another embodiment, the invention also relates to one or more of the invented compounds for use in the treatment or prevention of a bacterial infection or fungal infection or both bacterial and fungal infections in a subject.

In still another aspect, the invention is directed to a method of treating or preventing a bacterial infection or a fungal infection or both bacterial and fungal infections in a subject comprising administering a therapeutically effective amount of one or more of the compound of the invention to a subject in need thereof.

In still another aspect, the invention is directed to a compound or a composition of the invention for the removal/treatment of a biofilm or for inhibiting biofilm formation.

In yet another aspect, the invention also encompasses a method for producing a compound of the invention comprising (a) cultivating an organism of the genus *Xanthomonas* or *Burkholderia*; and (b) isolating said compound from said organism.

In another embodiment, the invention also relates to a method of producing a compound of the invention comprising reacting a compound of formula (VI)

(VI)

with a compound of formula (VII)

(VII)

under conditions to form a compound of the invention.

In still a further aspect, the invention relates to a mutant of *Xanthomonas campestris* pv. *campestris* strain XC1, producing any one of the compounds of the invention, wherein a Bmul5121 coding region of *Burkholderia multivorans* (ATCC 17616) or a homologue thereof has been inserted into the mutant.

DETAILED DESCRIPTION OF THE INVENTION

The present invention is based on the inventors' surprising findings that the compounds described herein are potent bactericidal and fungicidal compounds. The compounds are typically compounds of formula (I)

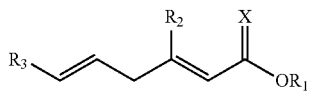 (I)

In this context, the term "alkyl" refers to a saturated aliphatic hydrocarbon including straight chain, or branched chain groups. Preferably, the alkyl group has 1 to 10 carbon atoms (whenever a numerical range; e.g., "1-10", is stated herein, it means that the group, in this case the alkyl group, may contain 1 carbon atom, 2 carbon atoms, 3 carbon atoms, etc. up to and including 10 carbon atoms). More specifically, it may be a medium size alkyl having 1 to 6 carbon atoms or a lower alkyl having 1 to 4 carbon atoms e. g., methyl, ethyl, n-propyl, isopropyl, butyl, iso-butyl, tert-butyl and the like. The alkyl group may be substituted or unsubstituted. When substituted, the substituent group(s) is one or more, for example one two, three, four or five groups, individually selected from the group consisting of $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, sulfinyl, sulfonyl, amino, and —$NR^{10}R^{11}$ where $R^{10}$ and $R^{11}$ are independently selected from the group consisting of hydrogen, $C_1$-$C_4$ alkyl, $C_3$-$C_8$ cycloalkyl, $C_6$-$C_{14}$ aryl, carbonyl, acetyl, sulfonyl, amino, and trifluoromethanesulfonyl, or $R^{10}$ and $R^{11}$, together with the nitrogen atom to which they are attached, combine to form a five-or six-membered heteroalicyclic ring.

The term "alkenyl" as used herein refers to an alkyl group that contains in the straight or branched hydrocarbon chain one or more double bonds. In certain embodiments, an alkenyl comprises 2 to 6 carbon atoms, for example 2 to 5 carbon atoms or 2 to 4 carbon atoms, wherein a numerical range, such as "2 to 6" or "$C_2$-$C_6$", refers to each integer in the given range, e.g. "$C_2$-$C_6$ alkenyl" means that an alkenyl group comprising 2 carbon atoms, 3 carbon atoms, etc., up to and including 6 carbon atoms. An alkenyl used in this invention can for example be substituted or unsubstituted. When substituted, the substituent group(s) is defined above. Examples of alkenyl groups include, but are not limited to, ethenyl, propenyl, butenyl, 1,4-butadienyl, pentenyl, 4-methylhex-1-enyl, 4-ethyl-2-methylhex-1-enyl and the like.

The term "alkynyl" as used herein refers to an alkyl group that contains in the straight or branched hydrocarbon chain one or more triple bonds. In certain embodiments, an alkynyl comprises 2 to 6 carbon atoms, for example 2 to 6 carbon atoms, 2 to 5 carbon atoms, or 2 to 4 carbon atoms, wherein a numerical range, such as "2 to 6" or "$C_2$-$C_6$", refers to each integer in the given range, e.g. "$C_2$-$C_6$ alkynyl" means that an alkynyl group comprising 2 carbon atoms, 3 carbon atoms, etc., up to and including 6 carbon atoms. An alkynyl group of this invention may be optionally substituted. Examples of alkynyl groups include, but are not limited to, ethynyl, propynyl, butynyl, and the like. An alkenyl group used in this invention can for example be substituted or unsubstituted. When substituted, the substituent group(s) can be defined as mentioned above.

The term "cycloalkyl" refers to a completely saturated hydrocarbon ring. The cycloalkyl group used in this invention may range from $C_3$ to $C_8$. A cycloalkyl group of this invention can for example be optionally substituted. Examples of cycloalkyl groups include, but are not limited to cyclopropyl, cyclobutyl, cyclopentyl, cyclohexyl and the like. An cycloalkyl group used in this invention can for example be substituted or unsubstituted. When substituted, the substituent group(s) can be defined as mentioned above.

The term "alkoxy", alone or in combination, refers to an aliphatic hydrocarbon having an alkyl-O-moiety. In certain embodiments, alkoxy groups are optionally substituted. Examples of alkoxy groups include, but are not limited to, methoxy, ethoxy, propoxy, butoxy and the like. An alkoxy group used in this invention can for example be substituted or unsubstituted. When substituted, the substituent group(s) can be defined as mentioned above.

A "cycloalkoxy" group refers to an —O-cycloalkyl group, as defined herein. One example is cyclopropyloxy. A cycloalkoxy group used in this invention can for example be substituted or unsubstituted. When substituted, the substituent group(s) can be defined as mentioned above.

An "aryl" group refers to an all-carbon monocyclic or fused-ring polycyclic (i.e., rings which share adjacent pairs of carbon atoms) groups of 6 to 14 ring atoms and having a completely conjugated pi-electron system. Examples, without limitation, of aryl groups are phenyl, naphthalenyl and anthracenyl. The aryl group may be substituted or unsubstituted. When substituted, the substituted group(s) is one or more, for example one, two, or three substituents, independently selected from the group consisting of $C_1$-$C_{10}$ alkyl, $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, trihalomethyl, carbonyl, thiocarbonyl, O-carbamyl, N-carbamyl, O-thiocarbamyl, N-thiocarbamyl, C-amido, N-amido, C-carboxy, O-carboxy, nitro, silyl, sulfinyl, sulfonyl, amino, and —$NR^{10}R^{11}$, with $R^{10}$ and $R^{11}$ as defined above. Preferably the substituent(s) is/are independently selected from chloro, fluoro, bromo, methyl, ethyl, hydroxy, methoxy, nitro, carboxy, methoxycarbonyl, sulfonyl, or amino.

A "heteroaryl" group refers to a monocyclic or fused aromatic ring (i.e., rings which share an adjacent pair of atoms) of 5 to 10 ring atoms in which one, two, three or four ring atoms are selected from the group consisting of nitrogen, oxygen and sulfur and the rest being carbon. Examples, without limitation, of heteroaryl groups are pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, isobenzofuryl, benzothienyl, benzotriazolyl, isobenzothienyl, indolyl, isoindolyl, 3H-indolyl, benzimidazolyl, benzothiazolyl, benzoxazolyl, quinolizinyl, quinazolinyl, pthalazinyl, quinoxalinyl, cinnnolinyl, napthyridinyl, quinolyl, isoquinolyl, tetrazolyl, 5,6,7,8-tetrahydroquinolyl, 5,6,7,8-tetra-hydroisoquinolyl, purinyl, pteridinyl, pyridinyl, pyrimidinyl, carbazolyl, xanthenyl or benzoquinolyl. The heteroaryl group may be substituted or unsubstituted. When substituted, the substituted group(s) is one or more, for example one or two substituents, independently selected from the group consisting of $C_1$-$C_{10}$ alkyl, $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, trihalomethyl, carbonyl, thiocarbonyl, O-carbamyl, N-carbamyl, O-thiocarbamyl, N-thiocarbamyl, C-amido, N-amido, C-carboxy, O-carboxy, nitro, silyl, sulfinyl, sulfonyl, amino, and —$NR^{10}R^{11}$, with $R^{10}$ and $R^{11}$ as defined above. Preferably the substituent(s) is/are independently selected from chloro, fluoro, bromo, methyl, ethyl, hydroxy, methoxy, nitro, carboxy, methoxycarbonyl, sulfonyl, or amino.

A "heteroalicyclic" group refers to a monocyclic or fused ring of 5 to 10 ring atoms containing one, two, or three heteroatoms in the ring which are selected from the group consisting of nitrogen, oxygen and —$S(O)_n$ where n is 0-2, the remaining ring atoms being carbon. The rings may also have one or more double bonds. However, the rings do not have a completely conjugated pi-electron system. Examples, without limitation, of heteroalicyclic groups are pyrrolidine, piperidine, piperazine, morpholine, imidazolidine, tetrahydropyridazine, tetrahydrofuran, thiomorpholine, tetrahydropyridine, and the like. The heteroalicyclic ring may be substituted or unsubstituted. When substituted, the substituted group (s) is one or more, for example one, two, or three substituents, independently selected from the group consisting of $C_1$-$C_{10}$ alkyl, $C_3$-$C_8$ cycloalkyl, $C_6$-$C_{14}$ aryl, 5-10 membered heteroaryl wherein 1 to 4 ring atoms are independently selected from nitrogen, oxygen or sulfur, 5-10 membered heteroalicyclic wherein 1 to 3 ring atoms are independently nitrogen, oxygen or sulfur, hydroxy, $C_1$-$C_{10}$ alkoxy, $C_3$-$C_8$ cycloalkoxy, aryloxy, mercapto, alkylthio, arylthio, cyano, halo, trihalomethyl, carbonyl, thiocarbonyl, O-carbamyl, N-carbamyl, O-thiocarbamyl, N-thiocarbamyl, C-amido, N-amido, C-carboxy, O-carboxy, nitro, silyl, sulfinyl, sulfonyl, amino, and —$NR^{10}R^{11}$, with $R^{10}$ and $R^{11}$ as defined above. The substituent(s) is/are for example independently selected from chloro, fluoro, bromo, methyl, ethyl, hydroxy, methoxy, nitro, carboxy, methoxycarbonyl, sulfonyl, or amino.

The term "heteroatom" refers to an atom other than carbon or hydrogen. Heteroatoms are typically independently selected from oxygen, sulphur, nitrogen, and phosphorus, but are not limited to those atoms. In embodiments in which two or more heteroatoms are present, the two or more heteroatoms may all be the same as one another, or some or all of the two or more heteroatoms may each be different from the others.

An "aryloxy" group refers to both an —O-aryl and an —O-heteroaryl group, as defined herein. Examples include and are not limited to phenoxy, napthyloxy, pyridyloxy, furanyloxy, and the like.

A "mercapto" group refers to an —SH group.

An "alkylthio" group refers to both an S-alkyl and an —S-cycloalkyl group, as defined herein. Examples include and are not limited to methylthio, ethylthio, and the like.

An "arylthio" group refers to both an —S-aryl and an —S-heteroaryl group, as defined herein. Examples include and are not limited to phenylthio, napthylthio, pyridylthio, furanylthio, and the like.

A "cyano" group refers to a —CN group.

A "halo" or "halogen" group refers to fluorine, chlorine, bromine or iodine.

A "trihalomethyl" group refers to a —$CX_3$ group wherein X is a halo group as defined herein e.g., trifluoromethyl, trichloromethyl, tribromomethyl, dichlorofluoromethyl, and the like.

"Carbonyl" refers to a —C(=O)—R" group, where R" is selected from the group consisting of hydrogen, alkyl, cycloalkyl, aryl, heteroaryl (bonded through a ring carbon) and heteroalicyclic (bonded through a ring carbon), as defined herein. Representative examples include and the not limited to acetyl, propionyl, benzoyl, formyl, cyclopropylcarbonyl, pyridinylcarbonyl, pyrrolidin-1ylcarbonyl, and the like.

A "thiocarbonyl" group refers to a —C(=S)—R" group, with R" as defined herein.

An "O-carbamyl" group refers to a —OC(=O)$NR^{10}R^{11}$ group, with $R^{10}$ and $R^{11}$ as defined herein.

An "N-carbamyl" group refers to a $R^{11}$OC(=O)$NR^{10}$— group with $R^{10}$ and $R^{11}$ as defined above.

An "O-thiocarbamyl" group refers to a —OC(=S)$NR^{10}R^{11}$ group, with $R^{10}$ and $R^{11}$ as defined above.

An "N-thiocarbamyl" group refers to a $R^{11}$OC(=S)$NR^{10}$— group, with $R^{10}$ and $R^{11}$ as defined above.

A "C-amido" group refers to a —C(=O)$NR^{10}R^{11}$ group, with $R^{10}$ and $R^{11}$ as defined herein. For example, $R^{10}$ is hydrogen or unsubstituted $C_1$-$C_4$ alkyl and $R^{11}$ is hydrogen, $C_1$-$C_4$ alkyl optionally substituted with heteroalicyclic, hydroxy, or amino. For example, C(=O)$NR^{10}R^{11}$ may be aminocarbonyl, dimethylaminocarbonyl, diethylaminocarbonyl, diethylaminoethylaminocarbonyl, ethylaminoethylaminocarbonyl, and the like.

A "nitro" group refers to a —$NO_2$ group.

A "sulfinyl" group refers to a —S(O)—R" group, wherein, R" is selected from the group consisting of hydrogen, hydroxy, alkyl, cycloalkyl, aryl, heteroaryl (bonded through a ring carbon) and heteroalicyclic (bonded through a ring carbon), as defined herein.

A "sulfonyl" group refers to a —$S(O)_2$R" group wherein R" is selected from the group consisting of hydrogen, hydroxy, alkyl, cycloalkyl, aryl, heteroaryl (bonded through a ring carbon) and heteroalicyclic (bonded through a ring carbon), as defined herein.

The compounds of and used in the invention are inclusive of all possible stereoisomers of the respective compounds, including tautomers, geometric isomers, e.g. Z and E isomers (cis and trans isomers), and optical isomers, e.g. diastereomers and enantiomers. Furthermore, the invention includes in its scope both the individual isomers and any mixtures thereof, e.g. racemic mixtures. In this context, the term "isomer" is meant to encompass all optical isomers of the compounds described herein. It will be appreciated by those skilled in the art that the compounds described herein may contain at least one chiral center. Accordingly, the compounds of the invention may exist in optically active or racemic forms. It is to be understood that the compounds according to the present invention may encompass any racemic or optically active form, or mixtures thereof. In one embodiment, the compounds of the invention can be pure (R)-isomers. In another embodiment, the compounds of the invention can be pure (S)-isomers. In another embodiment, the compounds of the invention can be a mixture of the (R) and the (S) isomers. In a further embodiment, the compounds of the invention can be a racemic mixture comprising an equal amount of the (R) and the (S) isomers. The individual isomers may be obtained using the corresponding isomeric forms of the starting material or they may be separated after the preparation of the end compound according to conventional separation methods. For the separation of optical isomers, e.g.

enantiomers, from the mixture thereof, the conventional resolution methods for example fractional crystallization may be used.

The compounds of the invention may also act as a prodrug. A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but then is metabolically hydrolyzed to the carboxylic acid, the active entity, once inside the cell where water solubility is beneficial. A prodrug may be converted into the parent drug by various mechanisms, including enzymatic processes and metabolic hydrolysis.

A further example of a prodrug might be a short polypeptide, for example, without limitation, a 2-10 amino acid polypeptide, bonded through a terminal amino group to a carboxy group of a compound of this invention wherein the polypeptide is hydrolyzed or metabolized in vivo to release the active molecule. The prodrugs of compounds of the invention are within the scope of this invention.

Additionally, it is contemplated that compounds of invention would be metabolized by enzymes in the body of the organism such as a human being to generate a metabolite that has an antibiotic or anti-microbial (anti-bacterial and/or anti-fungal) effect. Such metabolites are within the scope of the present invention.

As used herein, the term "pharmaceutically acceptable salt" refers to those salts which retain the biological effectiveness and properties of the parent compound. Such salts include, but are not restricted to: (1) an acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e. g., an alkali metal ion, such as sodium or potassium, an alkaline earth ion, such as magnesium or calcium, or an aluminum ion; or coordinates with an organic base such as ethanolamine, diethanolamine, triethanolamine, tromethamine, N-methylglucamine, and the like.

In some embodiments, the compounds of the invention can have the formula

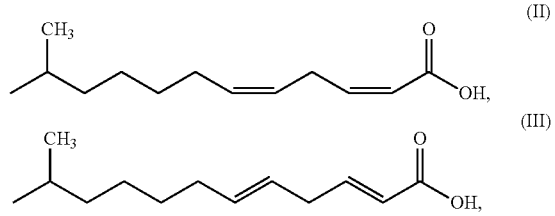

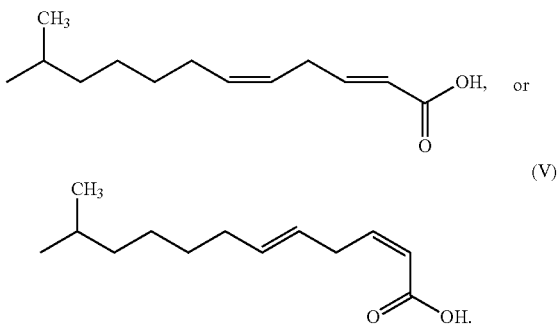

Utility

In one embodiment, the compounds of the invention can be used in a method for the treatment or prevention of a bacterial or fungal infection or both bacterial and fungal infections in a subject or an organism. In this context, the fungal infection can be caused by yeast or a non-yeast fungus. The fungal infection may, for example, be caused by fungi of the species *Candida albicans, Candida tropicalis, Candida (Clasvispora) lusitaniae, Candida (Pichia) guillermondii, Lodderomyces elongisporus, Debaryomyces hansenii, Pichia stipitis* (see also Rossignol T. et al, *Nucleic Acids Research*, 2008, 36:D557-D561), *Asperigillus fumigatus, Blastomyces dermatitidis, Cladophialophora bantiana, Coccidioides immitis, Cryptococcus neoformans, Fusarium* spp., *Microsporum* spp., *Penicillium marneffei* or *Trichophyton* spp. The bacterial infection may be caused by a Gram negative or a Gram positive bacterium. The bacterial infection may, for example, be caused by bacteria of the genus *Acinetobacter, Actinomyces, Aeromonas, Bordetella, Borrelia, Brucella, Burkholderia, Campylobacter, Chlamydia, Clostridium, Corynebacterium, Enterococcus, Erwinia, Escherichia, Francisella, Haemophilus, Helicobacter, Klebsiella, Legionella, Leptospira, Listeria, Mycobacterium, Mycoplasma, Neisseria, Pseudomonas, Rickettsia, Salmonella, Shigella, Staphylococcus, Streptococccus, Treponema, Veillonella, Vibrio* or *Yersinia*. In one particular embodiment, the infection is caused by *Staphylococcus aureus, Mycobacterium smegmatis, Pseudomonas aeruginosa, Burkholderia cepacia, Klebsiella pneumonia, Aeromonas hydrophila, Erwinia carotovora, Erwinia chrysanthemi,* or *Escherichia coli*. The subject affected by the bacterial and/or fungal infection may be a mammal, such as a human being.

In another embodiment the invention is directed to a compound or a composition of the invention for the removal/treatment of a biofilm or for inhibiting biofilm formation.

In this context it is noted that a wide variety of microorganisms, including both Gram-negative and Gram-positive bacteria, form and exist as biofilms under various conditions (Costerton et al., 1999; Sutherland, 2001). A biofilm is a complex aggregation of microbial cells marked by excretion of a protective and adhesive matrix. In most cases, a biofilm is recognized as a surface attached community with microbial cells interconnected by an extracellular matrix of polymeric substances, but occasionally non-attached or loosely attached bacterial cell aggregates can also be observed. Biofilm development can be divided into several key steps including attachment, microcolony formation, biofilm maturation and dispersion; and in each step bacteria may recruit different components and molecules including flagella, type IV pili, DNA and exopolysaccharides. Biofilm-forming bacteria pose severe problems in environment, industry and healthcare sectors due to increased bacterial survival competence in the environment and the protective nature of biofilms that prevents effective eradication. For example, bacterial biofilm associated chronic infections, and the medical device- and ship-associated biofilms are serious healthcare or industry problems (Costerton et al., 1999; O'Toole et al., 2000b; Donlan and Costerton, 2002; Parsek and Singh, 2003; see also An S. et al (2010), The Impact and Molecular Genetics of Bacterial Biofilms pages 212 to 226 in, Environmental Molecular Microbiology, Caister Academic Press, ISBN 978-1-904455-52-3).

In this context, it is noted that the term "biofilm or biofilms" are defined herein in accordance with its regular meaning in the art as an association of microorganisms growing attached to a surface and producing a slime layer of extracellular polymers in which the microbial consortia is embedded in a protective environment (for a review see: Costerton et al., Ann. Rev. Microbiol. 49: 711-45, 1995, An S et al, supra or see also International patent application WO 2003/039529). Biofilms represent a severe problem as bacteria integrated in such a polymer matrix develop resistance to conventional antimicrobial agents. *P. aeruginosa* cells, for example, growing in an alginate slime matrix have been demonstrated to be resistant to antibiotics (e. g., aminoglycosides, P-lactam antibiotics, fluoroquinolones) and disinfectants (Govan & Deretic, Microbiol. Rev. 60: 539-74, 1996). Several mechanisms for biofilm-mediated resistance development have been proposed (Costerton et al., Science 284: 1318-22, 1999).

In most natural, clinical and industrial settings bacteria are predominantly found in biofilms. Drinking water pipes, ship hulls, teeth or medical devices represent typical surfaces colonized by bacteria. On the one hand, biofilms decrease the life time of materials through corrosive action in the industrial field, a process also referred to as "biofouling". On the other hand two thirds of all bacterial infections in humans are associated with biofilms (Lewis, Antimicrob. Agents Chemother. 45: 999-1007, 2001). *Pseudomonas aeruginosa*, for example, forms infectious biofilms on surfaces as diverse as cystic fibrosis lung tissue, contact lenses, and catheter tubes (Stickler et al., Appl. Environm. Microbiol. 64: 3486-90, 1998). Thus, inhibition of biofilm formation of *P. aeruginosa* results in an impaired ability to form biofilms and therefore in an increased susceptibility to antibacterial treatment.

In this context, at least two types of cell-cell communication systems have been identified. The first one is quorum sensing, in which bacterial cells produce, detect and respond to small chemical signals to coordinate virulence gene expression and biofilm formation (Fuqua and Greenberg, 2002; Zhang and Dong, 2004; Dong and Zhang, 2005; He and Zhang, 2008). The second type is pathogen-host communication. For example, it has been revealed recently that the bacterial pathogen *Pseudomonas aeruginosa* can detect and respond to the polyamine signals from host to induce the expression of type III secretion system (Zhou et al., 2007), which is a key virulence determinant widely conserved in Gram-negative bacterial pathogens. Exogenous addition of AIPII, the autoinducing peptide signal produced by group II *S. aureus*, to the group I *S. aureus* cells reduces the skin lesion size on the inoculated mouse (Mayville et al., 1999). Expression of AHL-lactonase encoded by aiiA in transgenic tobacco and potato quenches the QS signaling of *E. carotovora* and significantly attenuates bacterial infection (Dong et al., 2001). DSF, which is the quorum sensing signal of *Xanthomonas campestris*, could be used for promoting biofilm dispersal (Dow et al. 2003; He et al., 2006), and for inhibition of the morphological transition of fungal pathogen *Candida albicans* (Wang et al., 2004). More recently, the signal BDSF from *Burkholderia cenocepacia*, which is a structural analogue of DSF, was shown to have dual roles against *C. albicans* by inhibiting morphological transition at a low concentration and killing the fungal cells at a high concentration (Boon et al., 2008).

The inventors found that the compounds of the present invention can, for example, prevent biofilm formation in *X. campestris*. In addition, the compounds of present invention can, for example, reduce the expression level of type III secretion system (T3SS) in *P. aeruginosa*. The compounds of the present invention can also inhibit *C. albicans* morphological transition.

In line with the above, the compounds of the present invention can, for example, be applied to the bacteria and fungi described above. In the following it is explained that the compounds of the present invention can be used as antibacterial and/or antifungal agents in various applications.

In a first embodiment, the compounds are useful for the treatment of mammalian in particular human diseases caused by bacteria through interference of bacterial physiology. Such diseases include endocarditis, respiratory and pulmonary infections (preferably in immunocompromized and cystic fibrosis patients), bacteremia, central nervous system infections, ear infections including external otitis, eye infections, bone and joint infections, urinary tract infections, gastrointestinal infections and skin and soft tissue infections including wound infections, pyoderma and dermatitis which all can be triggered by *Pseudomonas aeruginosa*, for example. Furthermore, the compounds can, for example, also be used for the treatment of pulmonary infections caused by *Burkholderia cepacia* (preferably in immunocompromized and cystic fibrosis patients), gastroenteritis and wound infections caused by *Aeromonas lçydrophila*, sepsis in tropical and subtropical areas caused by *Chrofnobacterium violaceum*, diarrhoea with blood and haemolytic uremic syndrome (HUS) caused by *Escherichia coli*, yersiniosis triggered by *Yersinia enterocolitica* and *Y. pseudotuberculosis*, and transfusion-related sepsis and fistulous pyoderma caused by *Serratia liquefaciens*, to name only a few.

The compounds of the invention can also be used to prevent and/or treat plant diseases, where interference of bacterial physiology reduces or abolishes virulence of bacterial plant pathogens. Such diseases include crown gall tumors caused by *Agrobacterium tumefaciens*, soft rot caused by *Burkholderia cepacia*, *Erwinia carotovora* and *Erwinia chrysanthemi*, sweet corn and maize infections caused by *Pantoea stewartii* and wilt disease caused by *Ralstonia solanacearum*. In another embodiment, the compounds can be used for the prevention and/or treatment of animal diseases, for example, fish diseases such as septicemia caused by *Aeromonas hydrophila* and *Vibrio anguillarum*, furunculosis in salmonids caused by *Aeromonas salmonicida*, prawn infections caused by *Vibrio harveyi* and enteric redmouth disease caused by *Yersinia ruckeri*, but also for the prevention and/or treatment of insect diseases caused, for example, by *Xenorhabdus nematophilus*.

The present invention also provides a method for reducing the virulence of bacterial pathogens employing, for example, but not limited to, an AHL-based signaling system. In one embodiment, a method is provided to remove, diminish, detach or disperse a bacterial biofilm from a living or nonliving surface by treating the surface with a compound of Formula (I). This method is also useful to prevent biofilm formation on a living or nonliving surface by treating the surface with a compound of Formula (I) before bacterial colonization can initialize. It is clear to persons skilled in the art, that the compounds of the present invention can be applied in a wide variety of different fields such as environmental, industrial and medical applications in order to prevent and/or treat damages or diseases caused by bacteria.

In one aspect, the compounds of the invention can be used for all kinds of surfaces in private and public areas, where it is beneficial to interfere Gram-negative or Gram-positive bacteria in order to prevent and/or treat colonization and biofilm formation. A compound of Formula (I) can be applied to the surface as a solution of the compound, alone or together with other materials such as conventional surfactants, preferably sodium dodecyl sulfate, or detergents, biocides, fungicides, antibiotics, pH regulators, perfumes, dyes or colorants. In combination with a bactericidal agent, e.g., the compounds of Formula (I) inhibit virulence or biofilm formation whilst the bactericidal agent kills the pathogens.

In one embodiment, the compounds can be used as antibacterial agent for topical use in cleaning and treatment solutions such as disinfectants, detergents, household cleaner and washing powder formulations in the form of a spray or a dispensable liquid. In one embodiment, these solutions can be applied to windows, floors, clothes, kitchen and bathroom surfaces and other surfaces in the area of food preparation and personal hygiene.

In addition, the compounds of the invention can be used as antibacterial ingredients in personal hygiene articles, toiletries and cosmetics. An example of such toiletries can include oral hygiene products. An oral hygiene product refers to any composition which is used in the mouth in order to promote oral hygiene. These compositions may be in the form of aqueous solutions, for example a mouth wash composition; gels, for example toothpaste or dentrifice compositions; solids, for example lozenges; or combined with fillers, for example chewing gum compositions. In this context, a dentrice refers to a paste, liquid or powder used to help maintain acceptable oral hygiene. Exemplary personal hygiene articles include but are not limited to soaps, shampoos, shower gels, ointments, creams, lotions, deodorants and disinfectants and storage solutions for contact lenses. Examples of cosmetics include foundation make-up, eye liner, lip stick, lip gloss to mention only a few. Therefore, in one embodiment, the present invention relates to a composition as described above, comprising the compounds of formula (I).

In another embodiment, the compounds can be used to prevent or treat bacterial biofilms in industrial settings such as ship hulls, paper manufacturing, oil recovery and food processing. The compounds can also be applied to water processing plants or drinking water distribution systems where the colonized surface (for example by *Pseudomonas aeruginosa*) may be the inside of an aqueous liquid system such as water pipes, water injection jets, heat exchangers and cooling towers. Until now biocides are the preferred tools to encounter these problems, but since biocides do not have a high specificity for bacteria, they are often toxic to humans as well. This can be circumvented by the application of a compound of the present invention.

In a further embodiment, the present invention relates to a method of inhibiting and/or preventing medical device-associated bacterial infections. The invention provides articles coated and/or impregnated with a compound of the invention in order to inhibit and/or prevent biofilm formation thereon. The articles may be surgical instruments, blood bag, systems or medical devices such as either permanently implanted devices such as artificial heart valves, prostethic joints, voice prosthesis, stents, shunts or not permanently implanted devices such as endotracheal or gastrointestinal tubes, pacemakers, surgical pins or indwelling catheters. Examples of indwelling catheters are urinary catheters, vascular catheters, peritoneal dialysis catheter, central venous catheters and needle-less connectors. The catheter materials can be polyvinylchloride, polyethylene, latex, Teflon®, polyurethane and silicone, a mixture thereof, or similar polymeric materials.

In this context it is noted that in order to reduce the risk of catheter-related bacterial infections, several catheters coated and/or impregnated with antiseptic or antimicrobial agents such as chlorhexidine/silver-sulfadiazine and minocycline/rifampin, respectively, have been developed. Furthermore, collection bags or layers sandwiched between an external surface sheath and a luminal silicone sheath have been constructed to overcome rapid loss of antimicrobial activity. Nevertheless, the emerging risk of bacterial resistance against traditional antibiotics limits the routine use of antibiotic-coated catheters.

The compounds of the invention, however, offer the possibility to effectively reduce catheter-related bacterial infections with a low risk of resistance development due to a novel therapeutic strategy targeting highly sensitive signal transduction mechanisms in bacteria. One form of application is the coating and/or impregnating of catheter materials on both the inner and outer catheter surfaces. The compounds of the invention may also be included in a mixture of antibacterial agents released continuously from a catheter-associated depot into the environment.

The present invention also provides a method for inhibiting, controlling or reducing morphological transition of fungal growth such as any of the fungi described above. In certain embodiments, the method of the invention also comprises inhibiting, controlling or reducing yeast-to-filamentous growth transition. As a non-limiting example, fungi such as those caused by *Candida albicans* (*C. albicans*) causes both superficial and disseminated (systemic) infections in humans. *C. albicans* is able to grow in different morphological forms, such as budding yeast (round or oval cells) and a range of filamentous forms that include true hyphae and pseudohyphae (Sudbeiy, P., N. Gow and J. Berman (2004), The distinct morphogenic states of *Candida albicans*. Trends Microbiol. 12:317-24). An essential component of the virulence of *C. albicans* is its ability to change between the yeast growth form and the filamentous growth forms. As used herein, the term "filamentous growth forms" includes both hyphal growth forms and pseudohyphal growth forms. Mutations that block transitions between these growth forms, and therefore restrict the organism to one of these two growth forms, also significantly reduce the virulence of the organism in mouse models of disseminated candidiasis (Lo et al., 1997; Braun et al., 2000; Saville et al., 2003; Zheng et al., 2003). Thus, one way of controlling fungal infections in humans may be to prevent or inhibit the yeast-to-filamentous growth transition through small bioactive molecules.

The inventors found that compounds of the invention can inhibit morphological transition (FIG. 4). In certain embodiments, the compounds of the invention can be used to treat fungal infections for example in subjects deemed medically of either having a fungal infection or being at significant risk of developing a fungal infection. A subject at risk of developing a fungal infection is a subject that has been exposed to a fungus or is susceptible to exposure to a fungus. For instance, subjects that are susceptible to exposure to a fungus includes those subjects who work in, live in or travel to areas with high fungal content or infectivity rates, as well as those subjects having particular susceptibility to fungal infection as a result of medical conditions or therapies. Examples of subjects having particular susceptibility to fungal infections arising from medical conditions or therapies include, but are not limited to, an immunocompromised subject (the compromised state of the subject's immune system could be the result of an infectious disease such as AIDS, an inherited disorder, or a treatment protocol for, but not limited to, cancer, organ transplants, or infectious diseases) or a subject having a central venous catheter.

Administration and Pharmaceutical Compositions

A compound of the present invention or a pharmaceutically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

As used herein, "administer" or "administration" refers to the delivery of a compound of formula (I), (II), (III), (IV) or (V) or a pharmaceutically acceptable salt thereof or of a pharmaceutical composition containing a compound of formula (I), (II), (III), (IV) or (V) or a pharmaceutically acceptable salt thereof of this invention to an organism for the purpose of prevention or treatment of a bacterial infection.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are oral and parenteral.

Alternatively, one may administer the compound in a local rather than systemic manner, for example, via injection of the compound directly into a vessel, optionally in a depot or sustained release formulation.

Pharmaceutical compositions of the present invention may be manufactured by processes well known in the art, e. g., by means of conventional mixing, dissolving, granulating, drageemaking, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatine, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatine, as well as soft, sealed capsules made of gelatine and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

The compounds may also be formulated for parenteral administration, e. g., by bolus injection or continuous infusion. Formulations for injection may be presented in unit dosage form, e. g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound.

Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextrane. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e. g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD:D5W) consists of VPD diluted 1:1 with a 5% dextrose in water solution. This cosolvent system dissolves hydrophobic compounds well, and itself produces low toxicity upon systemic administration.

Naturally, the proportions of such a co-solvent system may be varied considerably without destroying its solubility and toxicity characteristics. Furthermore, the identity of the co-solvent components may be varied: for example, other low toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for stabilization may be employed.

The pharmaceutical compositions herein also may comprise suitable solid or gel phase carriers or excipients. Examples of such carriers or excipients include, but are not limited to, calcium carbonate, calcium phosphate, various sugars, starch, cellulose derivatives, gelatine, and polymers such as polyethylene glycols.

Many of the compounds of the invention may be provided as physiologically acceptable salts wherein the claimed compound may form the negatively or the positively charged species. Examples of salts in which the compound forms the positively charged moiety include, without limitation, the sodium, potassium, calcium and magnesium salts formed by the reaction of a carboxylic acid or sulfonic acid group in the compound with an appropriate base (e.g. sodium hydroxide (NaOH), potassium hydroxide (KOH), Calcium hydroxide (Ca(OH)$_2$, etc.).

Pharmaceutical compositions suitable for use in the present invention include compositions wherein the active ingredients are contained in an amount sufficient to achieve the intended purpose, e. g., the treatment of a bacterial infection or fungal infection or both bacterial and fungal infections.

More specifically, a therapeutically effective amount means an amount of compound effective to prevent, alleviate or ameliorate symptoms of bacterial infection or fungal infection or both bacterial and fungal infections or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from the described assays. Then, the dosage can be formulated for use in animal models so as to achieve a circulating concentration range that includes the MIC as determined in the experiments (i.e., the minimum concentration of the test compound which achieves inhibition of bacterial or fungal growth). Such information can then be used to more accurately determine useful doses in humans.

Toxicity and therapeutic efficacy of the compounds described herein can be determined by standard pharmaceutical procedures in cell cultures or experimental animals, e.g., by determining the MIC and the $LD_{50}$ for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition.

Dosage amount and interval may be adjusted individually to provide plasma levels of the active species which are sufficient to maintain the anti-bacterial effect. These plasma levels are referred to as minimal effective concentrations (MECs).

Dosages necessary to achieve the MEC will depend on individual characteristics and route of administration. HPLC assays or bioassays can be used to determine plasma concentrations. Dosage intervals can also be determined using MEC value. Compounds should be administered using a regimen that maintains plasma levels above the MEC for 10-90% of the time, preferably between 30-90% and most preferably between 50-90%. In cases of local administration or selective uptake, the effective local concentration of the drug may not be related to plasma concentration and other procedures known in the art may be employed to determine the correct dosage amount and interval.

The amount of a composition administered may, of course, be dependent on the subject being treated, the severity of the affliction, the manner of administration, the judgment of the prescribing physician, etc.

The compositions may, if desired, be presented in a pack or dispenser device, such as a kit approved by a regulatory authority, such as EMEA or FDA, which may contain one or more unit dosage forms containing the active ingredient. The pack may for example comprise metal or plastic foil, such as a blister pack. The pack or dispenser device may be accompanied by instructions for administration.

The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration.

Compositions comprising a compound of the invention formulated in a compatible pharmaceutical carrier may also be prepared, placed in an appropriate container, and labeled for treatment of an indicated condition.

As used herein, a "physiologically/pharmaceutically acceptable carrier" refers to a carrier or diluent that does not cause significant irritation to an organism and does not abrogate the biological activity and properties of the administered compound.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatine, vegetable oils and polyethylene glycols.

Production

The invention also provides methods for producing a compound of the invention. These methods can comprise cultivating an organism of the genus *Xanthomonas* or *Burkholderia* and isolating said compound from *Xanthomonas* or *Burkholderia*. In some embodiments, the cultivating step may comprise incubation of the organism of *Xanthomonas* or *Burkholderia* in a yeast extract broth or minimal medium-as described in for example, Wang et al, 2004, *Mol Microbiol* 2004, 51: 903-912. The yeast broth may comprise Bacto tryptone, peptone, yeast extract, sucrose, NaCl, agar and/or magnesium sulfate. The minimal medium may comprise potassium phosphate, sodium sulfate, mannitol, glycerol, magnesium sulfate, ferrous sulfate, calcium chloride, and/or manganese chloride and may have a pH of 7.0. The cultivating step may be carried out for 24 hours and/or at 28° C.

The isolation of the compounds of the invention from the cultivated *Xanthomonas* or *Burkholderia* as defined above may comprise separation of the supernatant from the cells by column chromatography, centrifugation, basification of the supernatant, concentration of the supernatant by rotary evaporation, extraction of the supernatant by organic solvent, such as ethyl acetate, gel filtration chromatography of the extract, and/or reverse phase HPLC, such as reverse phase gradient HPLC.

In this context, the term "*Xanthomonas*" is used in accordance with its general meaning to refer to the genus that belongs to the family of Proteobacteria and that is known to cause plant diseases. The term "*Xanthomonas campestris* pv. *campestris*" refers to the species of the genus *Xanthomonas* which is known in the art and has been given the taxon identifier 340 (classification according to http://www.uniprot.org/taxonomy/340 (see also He, Y. W. et al, Genome scale analysis of diffusible signal factor regulon in *Xanthomonas campestris* pv. *campestris*: identification of novel cell-cell communication-dependent genes and functions. *Mol Microbiol.* 2006, 59: 610-622). The strain of the species *Xanthomonas campestris* pv. *campestris* that can be used to produce the compounds of the invention is XC1, as described in Wang, L. H. et al, A bacterial cell-cell communication signal with cross-kingdom structural analogues. *Mol Microbiol* 2004, 51: 903-912.

The term "*Burkholderia*" refers to the genus that also belongs to the family of Proteobacteria. In this context, suitable strains or the respective mutants of the genus *Burkholderia* that can be used to produce the compounds of the invention include *Burkholderia multivorans* (ATCC accession number 17616), *Burkholderia stabilis* (LMG accession number 14086), *Burkholderia anthina* (LMG accession number 16670) or *Burkholderia pyrrocinia* (LMG accession number 14191).

The invention also provides mutants of *Xanthomonas campestris* pv. *campestris* strain XC1, producing any one of the compounds of the invention. The term "mutant" when used in connection with the strain XC1 or *Burkholderia* defined above refers to a variant of the parental strain as well as methods for obtaining a mutant or variant in which the desired biological activity, i.e. the production of one or more compounds of formula (I) is similar or identical to that of the parental strain. The "parent strain" as defined herein is the original XC1 strain or the original *Burkholderia* strains defined above before mutagenesis. Mutants may occur in nature without the intervention of man. They are also obtainable by treatment with or by a variety of methods and compositions known to those of skill in the art. For example, the strain XC1 may be treated with a chemical such as N-methyl-N'-nitro-N-nitrosoguanidine, ethylmethanesulfone, or by irradiation using gamma, x-ray, or UV-irradiation, or by other means well known to those practiced in the art. A mutant strain or variant of XC1 can also be obtained by directed genetic engineering, for example, by overexpression or deletion or insertion of the genes encoding relevant enzymes or proteins. The mutants may be obtained to improve the yield of a compound of formula (I) or to cause the production of a modified compound of formula (I), meaning a compound of formula (I) that is different from the compound of formula (I) produced by the parental strain XC1. All such mutants and genetically engineered variants derived from the parental strain XC1 or the parental Burkholderia strains defined above are also encompassed by the present invention.

The compounds of the invention can also be produced by reacting a compound of formula (VI)

(VI)

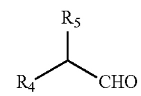

with a compound of formula (VII)

(VII)

under conditions to form a compound of the invention In the above synthesis, a carbonyl compound of formula (VI) is reacted with the carbanion of formula (VII) to yield an ester of formula (I). The resulting ester can be saponified using methods known in the art. The above synthesis can be adapted using the synthesis as described in Henrick C. A. et al, J. Agri. Food Chem., 1973. 21(3), 354-359 or U.S. Pat. No. 4,021,461, for example. The compounds of the invention can also be prepared using the well known "Wittig-Horner-Emmons-Reaction". In this context, the compounds of the present invention can also be prepared using or adapting the synthesis methods as described in Taber D. F. et al, J. Org. Chem. (2006), 71, 8973-8974. The compounds of formula (VI) and (VII) can be prepared using or adapting the synthesis as described in U.S. Pat. Nos. 3,163,669; 3,177,226; Davis, J. B., Jackman, L. M., Siddons, P. T., Weedon, B. C. L., J. Chem Soc. 2154 (1966); or Pattenden, G., Weedon, B. C. L., J. Chem. Soc. 1984 (1968)), for example. However, many of the aldehydes of formula (VI) such as heptanal, 6-methylheptanal (CAS Nr. 63885-09-6) or hexanal, to name only a few, are commercially available, or can be isolated from natural sources, for example.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The listing or discussion of a previously published document in this specification should not necessarily be taken as an acknowledgement that the document is part of the state of the art or is common general knowledge. All documents listed are hereby incorporated herein by reference in their entirety.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognise that the invention is also thereby described in terms of any individual member or subgroup of members of the Markush group.

EXAMPLES

Figure 1:
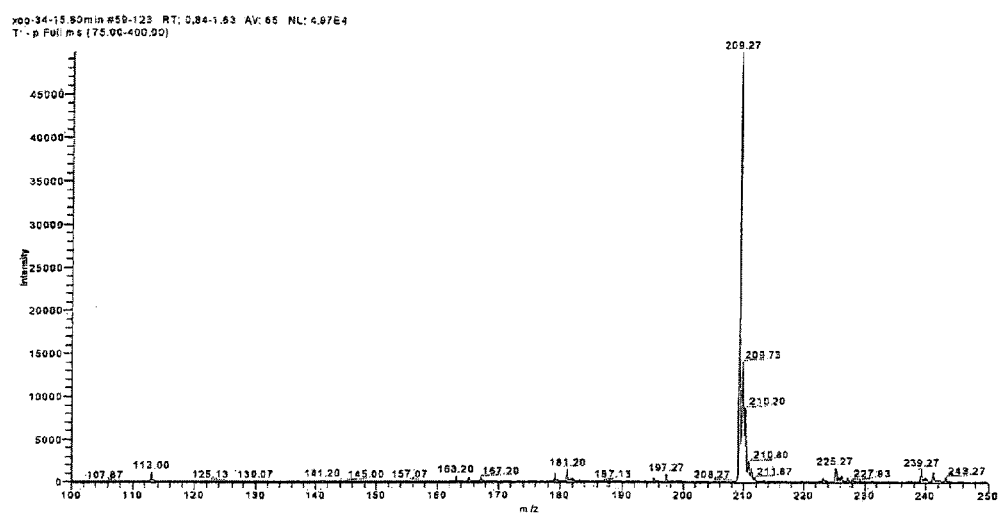
FIG. 1 shows ESI-MS and NMR analysis of purified cis-11-methyldodeca-2, 5-dienoic acid (MDEA). (a) ESI-MS spectrum of MDEA. (b) $^1$H NMR spectral of MDEA. (c) $^{13}$C NMR spectra of MDEA. (d) The deciphered chemical structure of MDEA.
Figure 1:
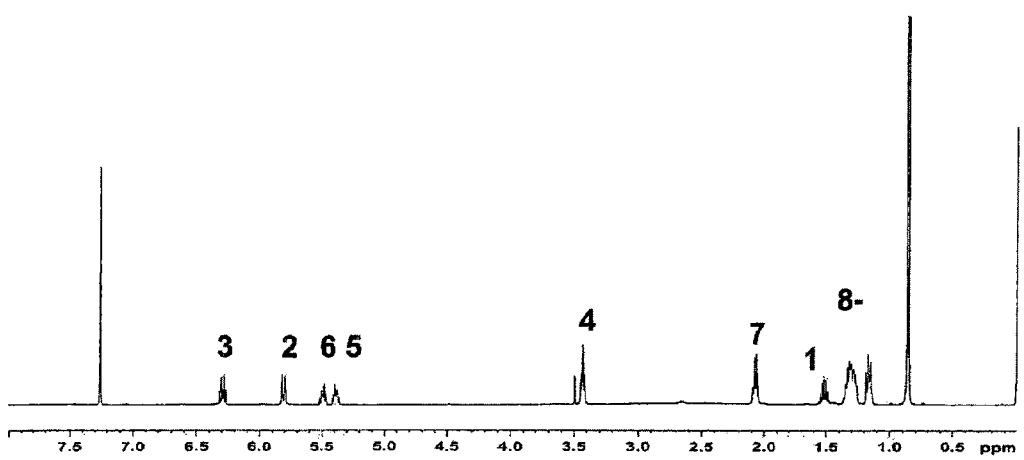
Figure 1:
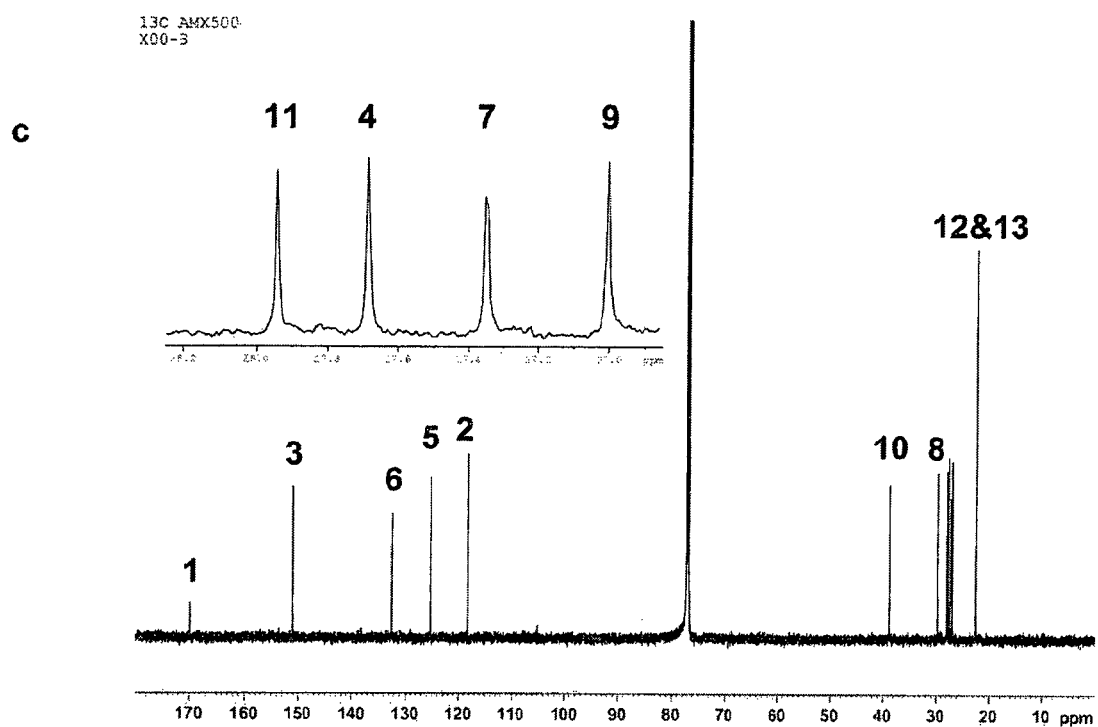
Figure 1:
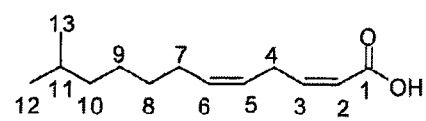

Bacterial strains and plasmids. *Xanthomonas campstris* pv. *campestris* strain XC1, its rpfC deletion mutant Xc1ΔC, have been previously described (Wang et al., 2004; He, Y. W et al, Dual Signaling Functions of the Hybrid Sensor Kinase RpfC of *Xanthomonas campestris* Involve Either Phosphorelay or Receiver Domain-Protein Interaction. *J. Biol. Chem.* 2006, 44: 33414-33421). *Burkholderia multivorans* ATCC17616, *B. stabilis* LMG 14086, *B. anthina* LMG 16670, and *B. pyrrocinia* LMG 14191 were reported previously (Mahenthiralingam et al., 2000; Rose et al., 2009). The broad-host-vector pLAFR3 was kindly provided by Allen Kerr. For production of DSF-like molecules, bacterial strains were grown in YEB medium (Wang et al., 2004) for about 24 h till OD600=3.0 at various temperatures as indicated in Table 1.

Engineering MDEA overproduction strains. The coding region of Bmul5121, which is the homologue of Xcc DSF coding gene rpfF (Wang et al., 2004), was amplified from *B. multivorans* via PCR using the primer pair Bmul5121-F (5'-ccggaattccggatgcagctccaatcacatccc) (SEQ ID NO: 1) and Bmul5121-R (5'-cccaagcttgggtcacaccgtgcgcaacttc) (SEQ ID NO: 2). The product was digested with EcoRI and HindIII and ligated to the broad-host-vector pLAFR3 at the same enzyme sites. The resultant construct was conjugated into the rpfC mutant Xc1ΔC by tri-parental mating. The transconjugants of Xc1ΔC containing the construct pLAFR3-Bmul5121 were selected on LB plates containing rifampicin and tetracycline and used for overproduction of MDEA.

Purification and structural characterization of MDEA. To identify novel DSF-like molecules from supernatants of different bacterial strains, the supernatant was acidified to pH 4.0 by diluted HCl and extracted by ethyl acetate (1.0 v/v) twice. After the ethyl acetate had been removed by rotary evaporation, the residue was subjected to flash chromatography on normal-phase silica gel, eluted with hexane (2 bed volume), 10% ethyl acetate in hexane (2 bed volume) and 25% ethyl acetate in hexane (4 bed volume). The active fractions, which were detected using the DSF sensor FE58 described previously (Wang et al., 2004), were combined for further HPLC profiling analysis. After evaporating the solvents, the residues were applied to HPLC (80% methanol in $H_2O$) on a reverse phase column (Phenomenex Luna 5μ $C_{18}$ 250×4.60 mm) and the peaks were monitored by UV detector with λ=210 and 254 nm at a flow rate of 1 ml min$^{-1}$. Fractions of one minute interval were collected and detected active molecules using the DSF bioassay.

The $^1$H, $^{13}$C and heteronuclear multiple quantum coherence (HMQC) nuclear magnetic resonance (NMR) spectra in CDCl$_3$ solution were obtained using a Bruker DRX500 spectrometer operating at 500 MHz for $^1$H or 125 MHz for $^{13}$C. High-resolution electrospray ionization mass spectrometry was performed on a Finnigan/MAT MAT 95XL-T mass spectrometer using the conditions described previously (Wang et al., 2004).

Biofilm assay. For analysis of biofilm formation, a single colony of *Xanthomonas campestris* strain 8004dF (He et al., 2006) was inoculated and grown overnight at 28° C. in 5 ml of YEB medium. The bacterial cells in culture were visualized with a phase contrast microscope (Olympus BX50) and photographs were taken with an Olympus DP70 digital camera.

Construction of reporter strain and measurement of β-galactosidase activity. The promoter of exsCEBA was amplified by PCR using the primer pairs pC-F/pC-R ((5'-gctctagacggt-gatccagtccttc (SEQ ID NO: 3)/5'-ggggcgcctcctaaagctc (SEQ ID NO: 4)), and cloned into the integration vector mini-CTX-lacZ (Zhou et al., 2007; Hoang et al., 2000; Becher and Schweizer, 2000). The construct was introduced into *E. coli* S17-1(λpir) and then integrated into the chromosome of *P. aeruginosa* as described previously (Hoang et al., 2000). The *P. aeruginosa* transconjugants were then selected on LB agar plates containing 100 μg/ml tetracycline and used as the T3SS reporter strain.

For determination of the inhibitory activity against T3SS, MDEA was added to the LB medium supplemented with 10 mM NTA before inoculation of the T3SS reporter strain. After incubation at 37° C. till $OD_{600}$ reached about 1.5, the bacterial cells were harvested by centrifugation to measure the β-galactosidase activities following the method previously described (Jeffrey, 1992).

RNA extraction and RT-PCR analysis. Bacteria were grown in LB medium supplemented with 10 mM NTA at 37° C. with shaking (250 rpm) overnight were diluted to an $OD_{600}$ of 0.05 in fresh LB medium and grown under the same conditions to an $OD_{600}$ of 1.5. RNA samples were isolated using the RNeasy mini kit according to the manufacturer's instructions (Qiagen). The concentration and purity of RNA were determined by spectrometry and agarose gel electrophoresis. RT-PCR analysis was performed using the One-step RT-PCR kit according to the manufacturer's instructions (Qiagen) with the primer pairs RT-C-F/RT-C-R ((5'-tggatttaacgagcaag-gtcaa (SEQ ID NO: 5), 5'-cgagaatctgcgcatacaactg (SEQ ID NO: 6)).

Microscopic analysis and quantification of *Candida albicans* germ tube formation. *C. albicans* strain SC5314 was incubated at 28° C. for overnight with shaking in the GMM medium consisting of 6.7 g of Bacto yeast nitrogen base (Difco) and 0.2% glucose (pH 7.2). *C. albicans* cells proliferate in yeast form under these conditions. The yeast cells were then diluted 20-fold in fresh GMM medium with or without MDEA. The cells were induced for 3 h at 37° C. Visualization and quantification of germ tube formation were performed using a phase contrast microscope (Olympus BX50) by counting about 400 *C. albicans* cells. The experiment was repeated twice, and the imaging was done with an Olympus DP70 digital camera.

Isolation of MDEA. The culture supernatants from different bacterial species were acidified to pH 4.0 with diluted HCl and extracted separately by ethyl acetate (1.0 v/v) twice. The organic solvent from each extract was removed by rotary evaporation, and the residues were subjected to a gradient flash chromatography on normal-phase silica gel and eluted by ethyl acetate in hexane from 0:100 to 25:75. The active fractions from the same bacterial species identified using bioassay were combined for HPLC analysis using a reverse phase column (Phenomenex Luna 5µ $C_{18}$ 250×4.60 mm) and 80% methanol (in water). The HPLC profile were monitored by UV detector with λ=210 and 254 nm, which led to identify a common peak (retention time: 16 min) conserved in Xcc strain XC1ΔC, *B. multivorans, B. stabilis, B. anthina*, and *B. pyrrocinia*. This common peak, which is different from the previously identified DSF and BDSF (Wang et al., 2004; Boon et al., 2008), was thus purified in large scale using the same flash chromatography and HPLC conditions for structural analysis.

Structure elucidation. Mass spectrometry (MS) analysis of this common molecule identified a molecular ion (M-H) with an m/z of 209.27 (FIG. 1*a*), which suggests two protons less than DSF (Wang et al., 2004). $^1H$ spectrum indicates that there are two pairs of ethylenic protons (FIG. 1*b*). The coupling constants between the protons in each pair are lower than 11 Hz. Therefore, the two double bonds are both in cis configuration (DSF only has one cis-double bond). Two methylene protons at $δ_H$ 3.45 suggest that this methylene carbon connects with the two double bonds. Overlapped signals of two doublet methyl group at $δ_H$ 0.87 exposed a branched structure same as DSF. $^{13}C$ spectra reveal that one of the double bonds conjugated with the carbolic acid (FIG. 1*c*). Therefore, the second double bond in the molecule should at C-5 (FIG. 1*d*). Collectively, the $^1H$, $^{13}C$ and HMQC data establish the structure of this active molecule as cis-11-methyldodeca-2, 5-dienoic acid (MEDA) (FIG. 1*d*).

Overexpression of rpfF to increase the yield of MDEA. The yield of MDEA produced by *Burkholderia* strains was rather low (Table 1). Deletion of rpfC in Xcc strain XC1 increased the MDEA yield from undetectable level to about 0.3 mg/L (Table 1). For increasing the yield, we cloned the rpfF homologue gene Bmul5121 from *B. multivorans* ATCC 17616 under the control of the constitutive promoter Plac in plasmid vector pLAFR3. The resultant construct pLAFR3-Bmul5121 was introduced into strain Xc1ΔC. The results showed that the engineered strain Xc1ΔC(5121) produced MDEA at a yield about 1.2 mg/L (Table 1), which is a 4-fold increment over the parental strain Xc1ΔC. In practice, all the rpfF homologues can be cloned in a multicopy vector, such as pLARF3, for overproduction of MDEA using Xcc or other suitable bacterial species as a host.

TABLE 1

The amount of MDEA purified from various bacterial strains

| Strains | Source or Characteristics | Growth Temperature | MDEA production (mg/L) |
|---|---|---|---|
| B. multivorans ATCC 17616 | Soil, USA | 37° C. | 0.025 |
| B. stabilis LMG 14086 | Respirator, UK | 28° C. | 0.015 |
| B. anthina LMG 16670 | Rhizosphere, UK | 28° C. | 0.002 |
| B. pyrrocinia LMG 14191 | Soil, Japan | 37° C. | 0.04 |
| XC1 | Wild type Xanthomonas campestris pv. campestris strain, China | 30° C. | Undetectable |
| Xc1ΔC | rpfC deletion mutant of Xanthomonas campestris pv. campestris strain XC1 | 30° C. | 0.3 |
| Xc1ΔC(5121) | Mutant Xc1ΔC harboring the expression construct pLAFR3-Bmul5121 | 30° C. | 1.2 |

Figure 2:
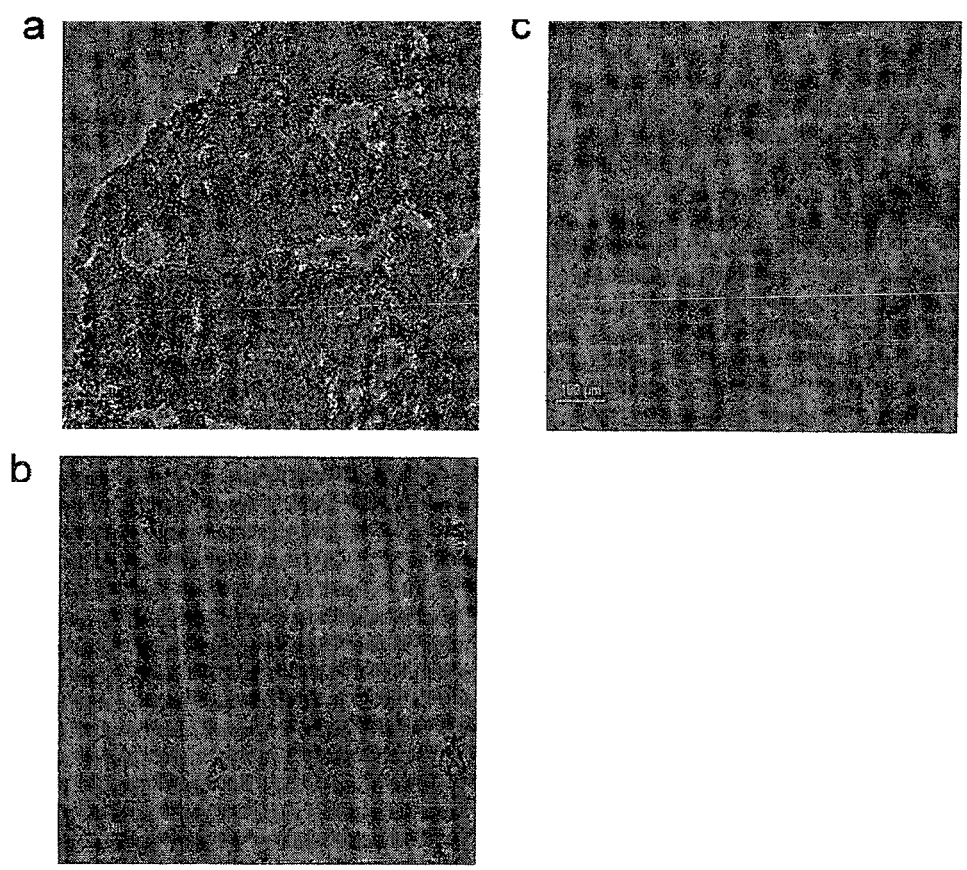
FIG. 2 shows Exogenous addition of MDEA promotes biofilm dispersal in Xcc DSF-deficient mutant 8004dF. (a) The DSF-deficient mutant 8004dF showed extensive biofilm formation. (b) Exogenous addition of 1 μM MDEA inhibited 8004dF biofilm formation. (c) Exogenous addition of 5 μM MDEA inhibited 8004dF biofilm formation.

MDEA controls Xcc biofilm formation. Given its structural similarity to DSF (Wang et al., 2004), which is known to regulate biofilm dispersal (Dow et al., 2003; He et al., 2006), MDEA was tested for its ability to promote Xcc biofilm dispersion. The Xcc DSF mutant ΔrpfF, which formed extensive cell aggregates (biofilm) in YEB medium (FIG. 2*a*), was used in this assay. The results showed that addition of 1 µM MDEA eliminated most of the cell aggregates (FIG. 2*b*). When the concentration of MDEA was increased to 5 µM, all the cell aggregates disappeared (FIG. 2*c*), suggesting that MDEA has similar activity as DSF in regulation of Xcc biofilm dispersal.

Figure 3:
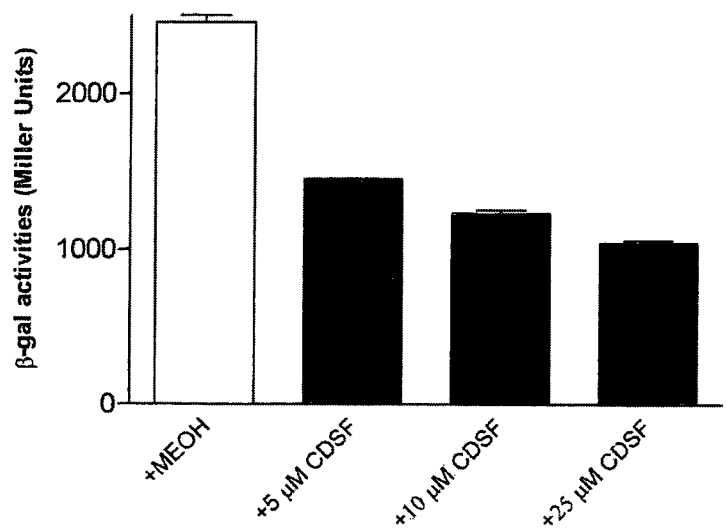
FIG. 3 shows Effect of MDEA (labeled as "CDSF") on the T3SS expression of *Pseudomonas aeruginosa*. The T3SS reporter strain containing the fusion gene PexsCEBA-lacZ was grown in LB medium supplemented with 10 mM NTA with or without MDEA until $OD_{600}$ reached 1.5. For each RNA sample, two dilutions (5, 50 ng) were used as templates for RT-PCT reaction with similar results obtained.
Figure 3:
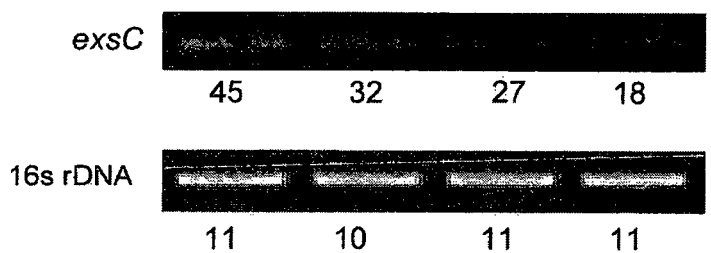

MDEA inhibits *P. aeruginosa* T3SS gene expression. Type III secretion system (T3SS) is a major virulence determinant conserved in many Gram-negative bacterial pathogens. To test the ability of MDEA on regulation of T3SS gene expression in *Pseudomonas aeruginosa*, the T3SS reporter construct PexsCEBA-lacZ (Zhou et al., 2007) was used. The promoter PexsCEBA directs the expression of the T3SS master regulator ExsA, which positively controls the expression of all T3SS genes in *P. aeruginosa* (Yahr and Wolfgang, 2006; Frank, 1997). The bioassay results showed that the expression of exsCEBA was inhibited by treatment with MDEA. Addition of 5 µM, 10 µM and 25 µM of MDEA to the bacterial culture resulted in 64.1%, 68.5% and 74.4% reduction of PexsCEBA-lacZ activity, respectively (FIG. 3*a*).

The effect of MDEA on inhibition of T3SS was further analyzed by semi-quantitative RT-PCR. The results showed that MDEA treatment of *P. aeruginosa* led to about 60% reduction in transcriptional expression of exsC (FIG. 3*b*). The data are consistent with the results based on the T3SS reporter (FIG. 3*a*).

Figure 4:
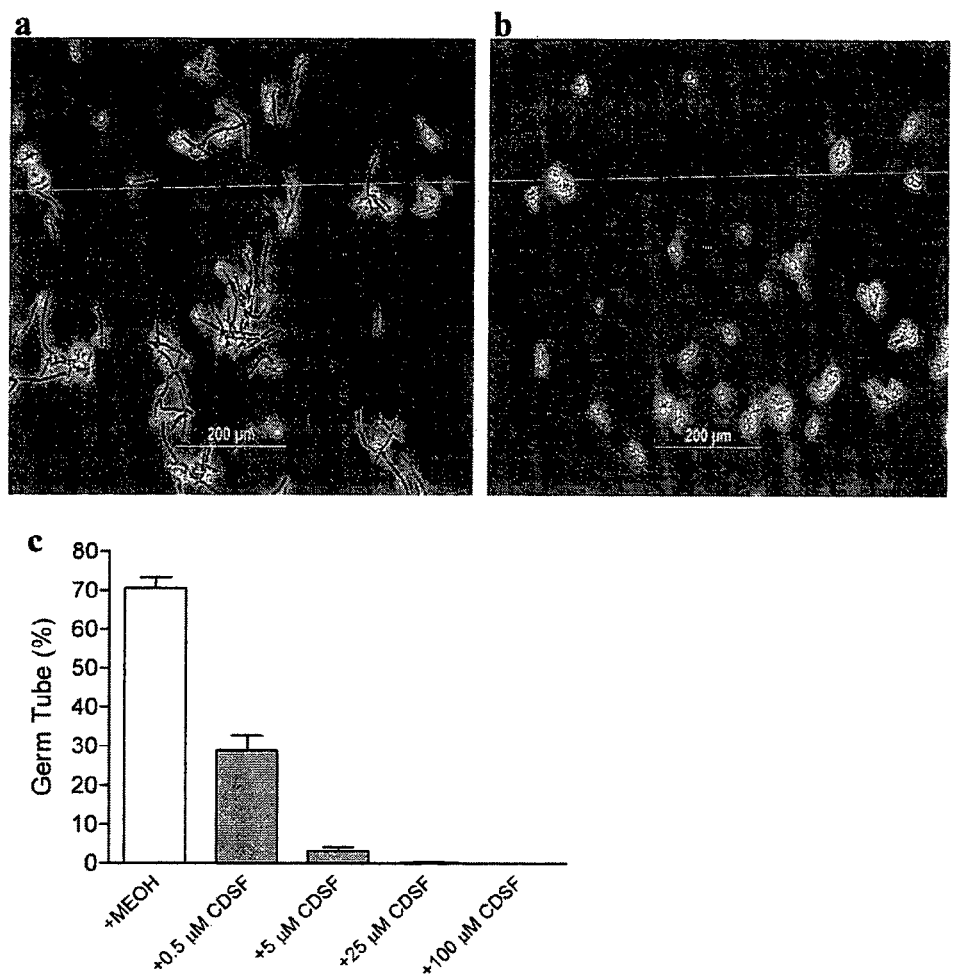
FIG. 4 shows Effect of MDEA on *C. albicans* germ tube formation. *C. albicans* cells were grown under inducing conditions (37° C.) without MDEA (a) or with 5 μM MDEA (b). The photos were taken 3 h after incubation. (c) Quantitative measurement of the inhibitory activity of MDEA (labeled as "CDSF") on germ tube formation of *C. albicans*. The experiment was performed twice and each time at least 400 cells were counted per treatment.

Inhibition of *C. albicans* morphological transition. *Candida albicans* is a fungal pathogen responsible for various forms of candiasis ranging from mucosal damages to serious systemic infections. It normally exists as a yeast but can form germ tubes (mycelia) under certain environmental conditions including human body temperature and serum. This morphological transition ability is critical for the fungal pathogen to establish infections. Mutants defective in morphological transitions are avirulent and unable to cause infections (Lo et al., 1997; Braun et al., 2000; Saville et al., 2003; Zheng et al., 2003). Several types of molecules were shown to inhibit the germ tube formation by C. albicans, including farnesoic acid produced by C. albicans (Oh et al., 2001), DSF from Xanthomonas campestris (Wang et al., 2004) and BDSF from Burkholderia cenocepacia (Boon et al., 2008). MDEA represents another structurally different unsaturated fatty acid. To determine its potential inhibitory activity MDEA was added to medium at various concentrations before inoculation of the fungal yeast cells, using methanol as a solvent control. After incubation at 37° C. for 3 h, about 70% of C. albicans cells in solvent control formed germ tubes (FIG. 4). In contrast, less than 30% and 5% of yeast cells could germinate in the presence of 0.5 or 5 µM of MDEA (FIG. 4). When the concentration was increased to 25 µM, the germ tube formation was reduced to 0.17% (FIG. 4). This data suggest that MDEA is a highly potent inhibitor of C. albicans morphological transition.

REFERENCES

An S. et al (2010), The Impact and Molecular Genetics of Bacterial Biofilms pages 212 to 226 in, Environmental Molecular Microbiology, Caister Academic Press, ISBN 978-1-904455-52-3.

Becher, A.; Schweizer, H. P. Integration-proficient Pseudomonas aeruginosa vectors for isolation of single-copy chromosomal lacZ and lux gene fusions. Biotech. 2000, 29: 948-952.

Boon, C.; Deng, Y.; Wang, L. H.; He, Y.; Xu, J. L.; Fan, Y.; Pan, S. Q.; Zhang, L. H. A novel DSF-like signal from Burkholderia cenocepacia interferes with Candida albicans morphological transition. ISME J. 2008, 2: 27-36.

Braun, B. R.; Head, W. S.; Wang, M. X.; Johnson, A. D. Identification and characterization of TUP1-regulated genes in Candida albicans. Genetics. 2000, 156: 31-44.

Costerton, J. W.; Lewandowski, Z.; Caldwell, D. E.; Korber, D. R.; Lappin-Scott, H. M. Microbial biofilms. Annu Rev Microbiol. 1995, 49: 711-45.

Davis, J. B., Jackman, L. M., Siddons, P. T., Weedon, B. C. L., J. Chem Soc. 2154 (1966)

Dong, Y. H.; Wang, L. H.; Xu, J. L.; Zhang, H. B.; Zhang, X. F.; Zhang, L. H. Quenching quorum-sensing-dependent bacterial infection by an N-acyl homoserine lactonase. Nature, 2001, 411: 813-817.

Dong, Y. H.; Zhang, L. H. Quorum sensing and quorum-quenching enzymes. J Microbiol. 2005, 43 (NO. S): 101-109.

Dow, J. M.; Crossman, L.; Findlay, K.; He, Y. Q.; Feng, J. X.; Tang, J. L. Biofilm dispersal in Xanthomonas campestris is controlled by cell-cell signaling and is required for full virulence to plants. Proc Natl Acad Sci USA. 2003, 100: 10995-11000.

Frank, D. W. The exoenzyme S regulon of Pseudomonas aeruginosa. Mol Microbiol. 1997, 26: 621-629.

Fuqua, C.; Greenberg, E. P. Listening in on bacteria: acyl-homoserine lactone signalling. Nat Rev Mol Cell Biol. 2002, 3: 685-695.

Govan & Deretic, Microbiol. Rev. 60: 539-74, 1996).

He, Y. W.; Xu, M.; Lin, K.; Ng, Y. J.; Wen, C. M.; Wang, L. H.; Liu, Z. D.; Zhang, H. B.; Dong, Y. H.; Dow, J. M.; Zhang, L. H. Genome scale analysis of diffusible signal factor regulon in Xanthomonas campestris pv. campestris: identification of novel cell-cell communication-dependent genes and functions. Mol Microbiol. 2006, 59: 610-622.

He, Y. W et al, Dual Signaling Functions of the Hybrid Sensor Kinase RpfC of Xanthomonas campestris Involve Either Phosphorelay or Receiver Domain-Protein Interaction. J. Biol. Chem. 2006, 44: 33414-33421.

He, Y. W.; Zhang, L. H. Quorum sensing and virulence regulation in Xanthomonas campestris. FEMS Microbiol Rev. 2008, 32: 842-857.

Hoang, T. T.; Kutchma, A. J.; Becher, A.; Schweizer, H. P. Integration-proficient plasmids for Pseudomonas aeruginosa: site-specific integration and use for engineering of reporter and expression strains. Plasmid. 2000, 43: 59-72.

International patent application WO 2003/039529

Jeffrey, H. M. A short course in bacterial genetics. Cold Spring Harbor Laboratory Press. 1992.

Lewis, Antimicrob. Agents Chemother. 45: 999-1007, 2001

Livermore, D. M. The need for new antibiotics. Clinical Microbiol. Infect. 2004, 10: 1-9.

Lo, H. J.; Kohler, J. R.; DiDomenico, B.; Loebenberg, D.; Cacciapuoti, A.; Fink, G. R. Nonfilamentous C. albicans mutants are avirulent. Cell. 1997, 90: 939-949.

Mahenthiralingam E, Bischof J, Byrne S K, Radomski C, Davies J E, Av-Gay Y, Vandamme P. DNA-Based Diagnostic Approaches for Identification of Burkholderia cepacia Complex, Burkholderia vietnamiensis, Burkholderia multivorans, Burkholderia stabilis, and Burkholderia cepacia Genomovars I and III J. Clin. Microbiol., 2000, 38(9): 3167-3173.

Mayville, P.; Ji, G.; Beavis, R.; Yang, H.; Goger, M.; Novick, R. P.; Muir, T. W. Structure-activity analysis of synthetic autoinducing thiolactone peptides from Staphylococcus aureus responsible for virulence. Proc Natl Acad Sci USA. 1999, 96: 1218-23

Oh, K. B.; Miyazawa, H.; Naito, T.; Matsuoka, H. Purification and characterization of an autoregulatory substance capable of regulating the morphological transition in Candida albicans. Proc Natl Acad Sci USA. 2001, 98: 4664-4668.

Pattenden, G., Weedon, B. C. L., J. Chem. Soc. 1984 (1968))

Pfaller, M. A.; Jones, R. N.; Doerm, G. V.; Kugler, K. Bacterial pathogens isolated from patients with bloodstream infection: frequencies of occurrence and antimicrobial susceptibility patterns from the SENTRY antimicrobial surveillance program (United States and Canada, 1997). Antimicrob Agents Chemother 1998, 42: 1762-1770.

Rose H, Baldwin A, Dowson CG, Mahenthiralingam E. Biocide susceptibility of the Burkholderia cepacia complex. J. Antimicrob. Chemother. 2009, 63(3): 502-510.

Rossignol T. et al, Nucleic Acids Research, 2008, 36:D557-D561.

Saville, S. P.; Lazzell, A. L.; Monteagudo, C.; Lopez-Ribot, J. L. Engineered control of cell morphology in vivo reveals distinct roles for yeast and filamentous forms of Candida albicans during infection. Eukaryot Cell 2003, 2: 1053-1060.

Stickler et al., Appl. Environm. Microbiol. 64: 3486-90, 1998

Sudbeiy, P., N. Gow and J. Berman (2004), The distinct morphogenic states of Candida albicans. Trends Microbiol. 12:317-24

Taber D. F. et al, J. Org. Chem. (2006), 71, 8973-8974

U.S. Pat. Nos. 3,163,669; 3,177,226;

Wang, L. H.; He, Y.; Gao, Y.; Wu, J. E.; Dong, Y. H.; He, C.; Wang, S. X.; Weng, L. X.; Xu, J. L.; Tay, L.; Fang, R. X.; Zhang, L. H. A bacterial cell-cell communication signal with cross-kingdom structural analogues. Mol Microbiol 2004, 51: 903-912.

Yahr, T. L.; Wolfgang, M. C. Transcriptional regulation of the Pseudomonas aeruginosa type III secretion system. Mol Microbiol 2006, 62: 631-640.

Zhang, L. H.; Dong, Y. H. Quorum sensing and signal interference: diverse implications Mol Microbiol 2004, 53: 1563-1571.

Zheng, X. D.; Wang, Y. M.; Wang, Y. CaSPA2 is important for polarity establishment and maintenance in *Candida albicans. Mol Microbiol* 2003, 49: 1391-1405.

Zhou, L.; Wang, J.; Zhang, L. H. Modulation of bacterial type III secretion system by a spermidine transporter dependent signaling pathway. *PLoS ONE* 2007, 2: e1291.

What is claimed is:

1. A method for producing a compound of formula (I) comprising reacting a compound of formula (VI)

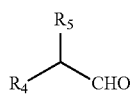
(VI)

with a compound of formula (VII)

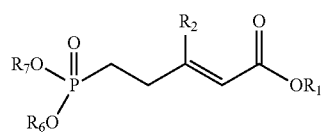
(VII)

under conditions to form the compound of formula (I), wherein $R^1$, $R^2$, $R^4$, $R^5$, $R^6$ and $R^7$ are independently selected from the group consisting of hydrogen, unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy, unsubstituted or substituted $C_6$-$C_{14}$ aryl, an unsubstituted or substituted 5- to 10-membered heteroaryl wherein 1 to 4 ring atoms are independently selected from nitrogen, oxygen or sulfur, an unsubstituted or substituted 5- to 10-membered heteroalicyclic ring wherein 1 to 3 ring atoms are independently nitrogen, oxygen or sulfur, —C(O)R, —C(O)OR, —C(O)NRR', —NRR', —S(O)$_2$R, —S(O)$_2$OR, and —S(O)$_2$NRR', R and R' are independently selected from the group consisting of hydrogen and unsubstituted or substituted $C_1$-$C_{10}$ alkyl, unsubstituted or substituted $C_1$-$C_{10}$ alkenyl, unsubstituted or substituted $C_1$-$C_{10}$ alkynyl;

or a tautomer, geometrical isomer, enantiomer, diastereomer, racemate form, pharmaceutically acceptable salt or prodrug thereof.

2. The method of claim 1, wherein $R^1$, $R^2$, $R^4$, $R^5$, $R^6$ and $R^7$ are independently selected from the group consisting of unsubstituted or substituted $C_1$-$C_{10}$ alkyl, unsubstituted or substituted $C_1$-$C_{10}$ alkenyl, unsubstituted or substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy.

3. The method of claim 2, wherein $R^1$, $R^2$, $R^4$, $R^5$, $R^6$ and $R^7$ is unsubstituted or substituted $C_1$-$C_{10}$ alkyl.

4. The method of claim 1, wherein the compound of formula (VI) is 2-methylpropanal, 3-methylbutanal, 4-methylpentanal, 3-methylhexanal, 6-methylheptanal, 6-methyloctanal, 7-methylnonanl or 9-methyldecanal.

* * * * *

UNITED STATES PATENT AND TRADEMARK OFFICE
CERTIFICATE OF CORRECTION

PATENT NO. : 8,785,680 B2
APPLICATION NO. : 13/697993
DATED : July 22, 2014
INVENTOR(S) : Lianhui Zhang et al.

It is certified that error appears in the above-identified patent and that said Letters Patent is hereby corrected as shown below:

In the claims, claim 1 should read:

1. A method for producing a compound of formula (I)

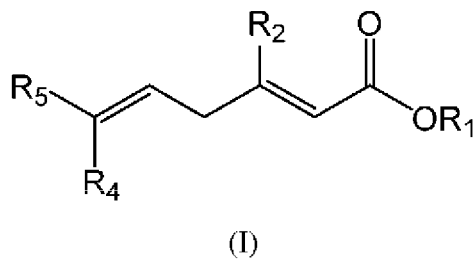

(I)

comprising reacting a compound of formula (VI)

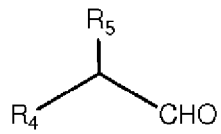

(VI)

with a compound of formula (VII)

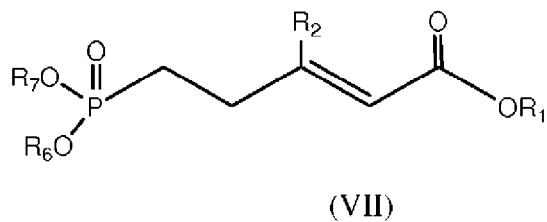

(VII)

under conditions to form the compound of formula (I),
wherein
$R^1$, $R^2$, $R^4$, $R^5$, $R^6$ and $R^7$ are independently selected from the group consisting of hydrogen, unsubstituted or substituted $C_1$-$C_{10}$ alkyl, unsubstituted or substituted $C_1$-$C_{10}$ alkenyl, unsubstituted or Signed and Sealed this
Third Day of November, 2015

Michelle K. Lee
*Director of the United States Patent and Trademark Office* substituted $C_1$-$C_{10}$ alkynyl, unsubstituted or substituted $C_3$-$C_8$ cycloalkyl, unsubstituted or substituted $C_1$-$C_{10}$ alkoxy, unsubstituted or substituted $C_3$-$C_8$ cycloalkoxy, unsubstituted or substituted $C_6$-$C_{14}$ aryl, an unsubstituted or substituted 5- to 10-membered heteroaryl wherein 1 to 4 ring atoms are independently selected from nitrogen, oxygen or sulfur, an unsubstituted or substituted 5- to 10-membered heteroalicyclic ring wherein 1 to 3 ring atoms are independently nitrogen, oxygen or sulfur, -C(O)R, -C(O)OR, -C(O)NRR', -NRR', -S(O)$_2$R, -S(O)$_2$OR, and -S(O)$_2$NRR', R and R' are independently selected from the group consisting of hydrogen and unsubstituted or substituted $C_1$-$C_{10}$ alkyl, unsubstituted or substituted $C_1$-$C_{10}$ alkenyl, unsubstituted or substituted $C_1$-$C_{10}$ alkynyl;

or a tautomer, geometrical isomer, enantiomer, diastereomer, racemate form, pharmaceutically acceptable salt or prodrug thereof.

```
                              SEQUENCE LISTING

<160> NUMBER OF SEQ ID NOS: 6

<210> SEQ ID NO 1
<211> LENGTH: 33
<212> TYPE: DNA
<213> ORGANISM: artificial
<220> FEATURE:
<223> OTHER INFORMATION: Bmul5121-F primer

<400> SEQUENCE: 1
ccggaattcc ggatgcagct ccaatcacat ccc                                33

<210> SEQ ID NO 2
<211> LENGTH: 31
<212> TYPE: DNA
<213> ORGANISM: artificial
<220> FEATURE:
<223> OTHER INFORMATION: Bmul5121-R primer

<400> SEQUENCE: 2
cccaagcttg ggtcacaccg tgcgcaactt c                                  31

<210> SEQ ID NO 3
<211> LENGTH: 25
<212> TYPE: DNA
<213> ORGANISM: artificial
<220> FEATURE:
<223> OTHER INFORMATION: pC-F primer

<400> SEQUENCE: 3
gctctagacg gtgatccagt ccttc                                         25

<210> SEQ ID NO 4
<211> LENGTH: 19
<212> TYPE: DNA
<213> ORGANISM: artificial
<220> FEATURE:
<223> OTHER INFORMATION: pC-R primer

<400> SEQUENCE: 4
ggggcgcctc ctaaagctc                                                19

<210> SEQ ID NO 5
<211> LENGTH: 22
<212> TYPE: DNA
<213> ORGANISM: artificial
<220> FEATURE:
<223> OTHER INFORMATION: RT-C-F primer

<400> SEQUENCE: 5
tggatttaac gagcaaggtc aa                                            22

<210> SEQ ID NO 6
<211> LENGTH: 22
<212> TYPE: DNA
<213> ORGANISM: artificial
<220> FEATURE:
<223> OTHER INFORMATION: RT-C-R primer

<400> SEQUENCE: 6
cgagaatctg cgcatacaac tg                                            22
```